US008777887B2

(12) United States Patent
Jönsson et al.

(10) Patent No.: US 8,777,887 B2
(45) Date of Patent: Jul. 15, 2014

(54) MEDICAL APPARATUS

(75) Inventors: Lars Jönsson, Arlöv (SE); Riccardo Pellegrini, Foggia (IT); Andrea Ligabue, San Prospero (IT)

(73) Assignee: Gambro Lundia AB, Lund (SE)

( * ) Notice: Subject to any disclaimer, the term of this patent is extended or adjusted under 35 U.S.C. 154(b) by 346 days.

(21) Appl. No.: 12/680,451

(22) PCT Filed: Oct. 3, 2007

(86) PCT No.: PCT/IB2007/002914
§ 371 (c)(1),
(2), (4) Date: May 14, 2010

(87) PCT Pub. No.: WO2009/044220
PCT Pub. Date: Apr. 9, 2009

(65) Prior Publication Data
US 2010/0312161 A1    Dec. 9, 2010

(51) Int. Cl.
*A61M 1/16* (2006.01)
(52) U.S. Cl.
CPC ......... *A61M 1/16* (2013.01); *A61M 2205/3317* (2013.01); *Y10S 128/908* (2013.01)
USPC .................... 604/5.01; 604/6.16; 128/303.13; 128/908
(58) Field of Classification Search
USPC ........... 604/4.01, 5.01, 6.16; 128/303.13, 908
See application file for complete search history.

(56) References Cited

U.S. PATENT DOCUMENTS

| | | | |
|---|---|---|---|
| 3,963,981 A * | 6/1976 | Vis ................................. | 324/510 |
| 4,788,977 A | 12/1988 | Farin et al. | |
| 6,882,511 B1 * | 4/2005 | Patruno et al. ................... | 361/42 |
| 7,209,651 B1 * | 4/2007 | Knoeppel et al. ............. | 392/451 |
| 2003/0220599 A1 * | 11/2003 | Lundtveit et al. ............ | 604/5.01 |

FOREIGN PATENT DOCUMENTS

| | | |
|---|---|---|
| GB | 2 177 309 A | 1/1987 |
| WO | 2004/108206 A1 | 12/2004 |
| WO | WO 2004108206 A1 * | 12/2004 ............. A61M 39/10 |

OTHER PUBLICATIONS

Jonsson P. et al., "Blood lines conduct leakage current during haemodialysis: a potential safety risk during first failure, especially for patients with central dialysis catheter as access", Medical & Biological Engineering & Computing Nov. 2005, vol. 43, No. 6, Nov. 2005, pp. 731-738, XP002488175, ISSN: 0140-0118.

* cited by examiner

*Primary Examiner* — Leslie Deak
*Assistant Examiner* — Sara Sass
(74) *Attorney, Agent, or Firm* — Pearne & Gordon LLP (57) ABSTRACT

In a hemodiafiltration apparatus, a membrane device (2) comprises a blood chamber (3) and a fluid chamber (4) separated by a semipermeable membrane (5). A grounding device (17) is connected to the discharge line by means of a tubular connector (16) made of an electrically-conductive plastic material. The grounding device can disconnect the grounding connection if the leakage current measured on a patient (1) connected to the apparatus exceeds a predetermined value. The apparatus can be classified as Cardiac Floating and, at the same time, causes no disturbances to an electrocardiograph connected to the patient.

25 Claims, 6 Drawing Sheets

MEDICAL APPARATUS

BACKGROUND OF THE INVENTION

The invention relates to a medical apparatus, in particular an apparatus for extracorporeal blood treatment or an infusion apparatus.

Specifically, though not exclusively, the invention can be usefully applied in medical apparatus where a high level of electrical safety is required for the patient, for example in an apparatus for intensive treatment of kidney and/or hepatic insufficiency and/or cardiac failure (renal and/or hepatic and/or heart intensive care), or in other intensive care units, or in other medical units for chronic treatment of patients.

The prior art comprises patent publication WO 2004/108206, which describes a medical apparatus provided with a system for reduction of the disturbance caused to an electrocardiograph by effect of the normal functioning of the apparatus itself. The system comprises a grounding device connected to at least a fluid transport line of the medical apparatus by means of a tubular connector made of an electrically-conductive plastic material. The grounding device grounds the static electrical charges which might disturb the correct functioning of an electrocardiograph connected up to the patient.

The apparatus of WO 2004/108206, however, exhibits the drawback that the grounding device might prevent the insulation required for some parts of the apparatus applied to the patient in order for it to obtain the Cardiac Floating (CF) classification. Some medical apparatus, especially those having some parts applied close to the patient's heart (for example in a case which includes a central venous catheter), must have a CF classification in order to respect a number of standards relating to a patient's electrical safety.

On the other hand, a medical apparatus having the CF classification, being characterized by a high degree of electrical insulation, i.e. a high level of impedance between the grounding protection and the part of the apparatus applied to the patient, is unable to dissipate the static charges which disturb the operation of the electrocardiograph applied to the patient.

SUMMARY OF THE INVENTION

An aim of the present invention is to provide a medical apparatus which obviates the above-described limits and drawbacks.

A further aim of the invention is to provide a medical apparatus having a high level of electrical safety for the patient.

A further aim of the invention is to reduce the disturbance caused by electrical charges generated by the medical apparatus to an external system, for example an electrocardiograph applied to the patient.

An advantage of the invention is to provide an apparatus which is constructionally simple and economical.

A further advantage of the invention is to make available a grounding system for a medical apparatus which is particularly applicable to apparatus provided with peristaltic pumps for fluid transport (the patient's blood, infusion fluid, dialysis fluid, replacement fluid, etc), or provided with other organs generating static charges which can cause disturbance to another system connected to the patient.

These aims and more besides are all attained by the present invention, as it is characterized by one or more of the appended claims.

In a specific embodiment of the invention, the medical apparatus is provided with a grounding system able to modify its own impedance according to the current in the patient or in a part of the apparatus itself. In this way the medical apparatus can be connected to the ground with a relatively low impedance level (such as also to disperse any electrical charges which might disturb a system connected to the patient or the medical apparatus, such as for example an electrocardiograph), while at the same time the medical apparatus exhibits a high level of electrical safety (such as for example to be classifiable as Cardiac Floating) since as soon as the charges reach a predetermined risk level, the apparatus is insulated from the earth by virtue of an increase in the impedance level of the grounding connection. The insulating configuration is maintained as long as the charges are relatively high or for a predetermined time (for example for a fraction of a second), or until the next power on, after which the lower-impedance grounding configuration is reset, such as to enable correct functioning of the system connected to the patient or the medical apparatus (e.g. the electrocardiograph).

In a specific embodiment of the invention, the grounding system of the medical apparatus comprises a grounding line provided with two or more resistances in series, at least one of which can be short-circuited or opened by means of a switch (for example any relay of known type) activated on command, for example, of an electrical circuit or a programmed processor.

In a specific embodiment of the invention, the grounding system comprises a comparator which compares a signal indicating an electrical property (for example current or voltage) applied to the patient or to an apparatus connected to the patient, with a reference value (for example a threshold value indicating a risk for the electrical safety of the patient), and sends an output signal as a result of the above comparison. The output signal can be used to vary the configuration of the grounding system.

In a specific embodiment of the device, the grounding system of the medical device has a variable configuration (being able to assume at least two different configurations), and further comprises a sensor designed to provide a signal indicating an electrical value (for example current or voltage) applied to the patient or to a device connected to the patient. The signal can be used to monitor the patient's electrical safety and consequently to modify the configuration of the grounding system. If the signal indicates that the patient is in an electrical safety situation, the grounding system is consequently configured such as to be able to eliminate any disturbance to external systems connected to the patient (for example an electrocardiograph) caused in particular by static charges. If, on the other hand, the signal indicates that the patient is in a risky situation as regards electrical power, the grounding system is consequently configured such as to bring the patient into a safety condition (for example putting the grounding system into a configuration of ground-insulation).

In a specific embodiment of the invention, the grounding system of the medical apparatus can assume (for example on command of an electrical circuit or a programmed processor) at least two different configurations. In a first configuration the grounding system is substantially grounded, while in a second configuration the system is substantially disconnected from the ground or connected via a very high impedance. The selection of one or the other configuration is performed on the basis of monitoring of a measurement indicating the patient's safety level.

In a specific embodiment of the invention, the grounding system is connected to the medical apparatus via an electrically-conductive part of a fluid transport system (for example a medical fluid circuit or a biological fluid circuit or a used treatment fluid circuit). The electrically-conductive part (made for example of a plastic material with an electrically-conductive additive) exhibits a higher electrical conductivity than the rest of the fluid transport system. The electrically-conductive part can comprise a tubular element inserted in a tract of the fluid path of the circuit.

Further characteristics and advantages of the present invention will better emerge from the detailed description that follows, of at least an embodiment of the invention, illustrated by way of non-limiting example in the accompanying figures of the drawings.

BRIEF DESCRIPTION OF THE DRAWINGS

The description will be made with reference to the accompanying figures of the drawings, which are provided by way of non-limiting example, in which.

DETAILED DESCRIPTION

Figure 1:
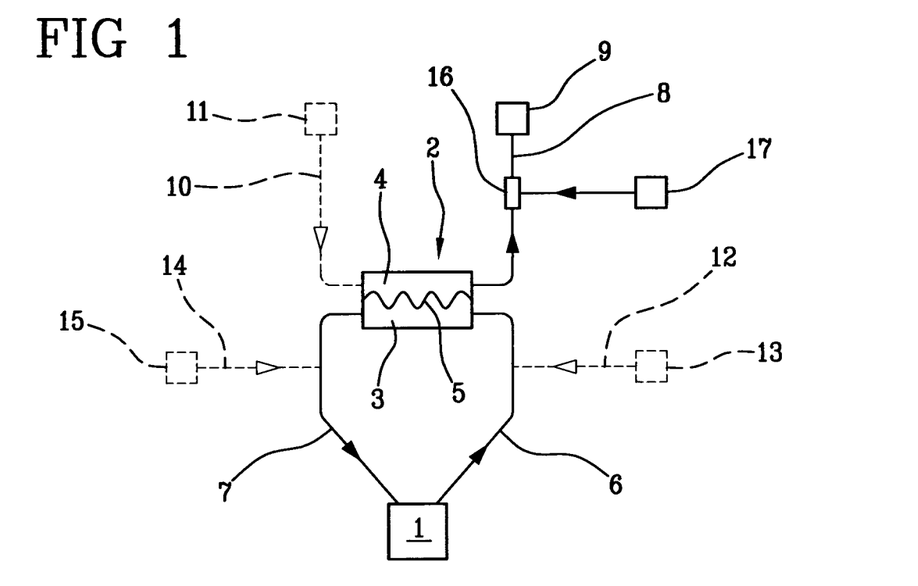
FIG. 1 shows a first embodiment of a medical apparatus of the present invention.

FIG. 1 shows an apparatus for extracorporeal blood treatment connected to the cardiovascular system of a patient 1 via a vascular access device (of known type). The treatment apparatus comprises a membrane device 2 having a blood chamber 3 and a fluid chamber 4 which are separated from one another by a semipermeable membrane 5. The membrane device 2 is connected to the patient 1 by means of an extracorporeal blood circuit which comprises a withdrawal line 6 and a return line 7. The withdrawal line 6 is configured to transport the patients' blood to the blood chamber 3 where it is subjected to the treatment. The return line 7 is configured to return the blood from the blood chamber 3 to the patient 1.

The treatment apparatus further comprises a fluid circuit connected to the fluid chamber 4. The fluid circuit comprises a discharge line 8 which connects the fluid chamber 4 to a drainage 9. The drainage 9 can comprise, for example, one or more collection bags for the used fluid. The used fluid can contain, for example, a quantity of liquid ultra-filtered from the blood across the semi-permeable membrane 5.

The treatment apparatus can further comprise a supply line 10 which connects the fluid chamber 4 with a source of fresh treatment fluid 11 (for example a dialysis fluid). In this case the used fluid sent to the drainage 9 will comprise the used treatment fluid at the outlet of the fluid chamber 4. The source of fresh treatment fluid 11 can comprise, for example, one or more bags of liquid.

The treatment apparatus can further comprise at least an upstream infusion line 12 which connects the withdrawal line 6 with one or more sources of infusion fluid 13 (for example a substitution fluid in a hemofiltration treatment, and/or an anticoagulant fluid, and/or a medical fluid). The upstream infusion line 12 opens into the extracorporeal blood circuit upstream of the membrane device 2. The treatment apparatus can further comprise at least a downstream infusion line 14 which connects the return line 7 with one or more sources of infusion fluid 15 (for example a substitution fluid in a hemofiltration treatment, and/or a medical fluid). The downstream infusion line 14 opens into the extracorporeal blood circuit downstream of the membrane device 2.

Note that each of the following elements: the supply line 10, the fresh treatment fluid source 11, the upstream infusion line 12, the downstream infusion line 14 and the infusion sources 13 and 15 (all indicated by broken lines in FIG. 1), is a non-compulsory element, i.e. not necessary and therefore possibly not present in the treatment apparatus.

The treatment apparatus comprises an electrically conductive element which in the specific case is made in the form of a tubular connector 16 inserted in the discharge line 8. The tubular connector 16 constitutes, in substance, a relatively short tract of the line itself. The tubular connector 16 has a greater electrical conductivity than the rest of the discharge line. The tubular connector 16 is configured for transporting electrical charges from the internal surface thereof to the external surface thereof. The tubular connector 16 is made of an electrically conductive material, for example a plastic material with a carbon-based additive. In particular the tubular connector 16 can comprise a conductive joint such as one of those described or claimed in patent publication WO 2004/108206, which is incorporated herein for reference.

The treatment apparatus further comprises a grounding device 17 for connecting the tubular connector 16. The grounding device 17 is connected to the tubular connector 16 by a connecting device comprising a support element similar to the support element denoted by 44 in the description and in the figures of patent publication WO 2004/108206, which are to be considered as incorporated herein for purposes of reference, or by the support element described in claim 34 of the same patent publication, WO 2004/108206, which is also to be considered as incorporated herein for purposes of reference.

The grounding device 17 can comprise any one of the grounding devices which will be described in the following, with reference to figures from 4 to 7.

Figure 4:
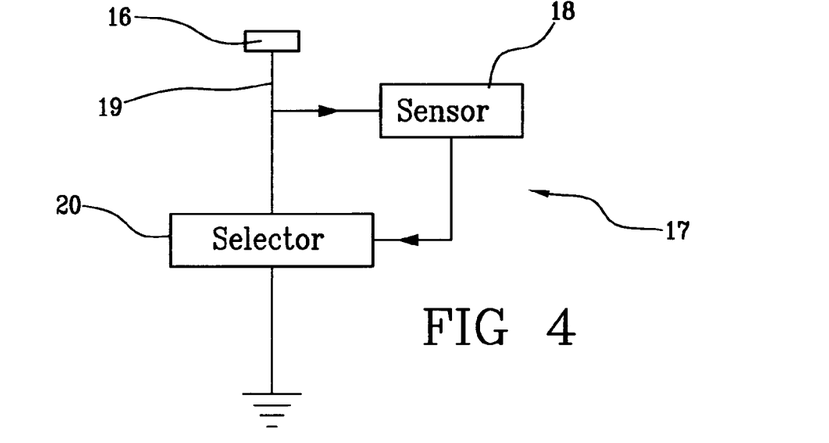
FIG. 4 is a first embodiment of a grounding device which can be used in the medical apparatus of the invention.

In FIG. 4, the grounding device 17 comprises a sensor 18 configured to be sensitive to a parameter indicative of an electrical current along a grounding line 19 which connects the tubular connector 16 with the ground. The parameter is also indicative of the intensity of the electrical current leaked from the patient, i.e. the electrical current leaked onto the parts of apparatus connected to the patient. The sensor 18 is connected to a selector 20 which is configured to vary the electrical resistance of the grounding line 19 according to the value of the above-mentioned parameter detected by the sensor 18. In particular the sensor 18 and the selector 20 are configured such that when the parameter detected by the sensor indicates that the leakage current is less than a predetermined threshold value, the selector assumes a first configuration in which the connection between the medical apparatus and the ground has a first impedance value, while when the parameter detected by the sensor indicates that the leakage current is greater than a predetermined threshold value, the selector assumes a second configuration in which the connection between the medical apparatus and the ground has a second impedance value which is greater than the first. In a specific example, as soon as the leakage current exceeds a certain threshold level, the medical apparatus (the parts thereof connected to the patient) is substantially insulated from the ground (first configuration with a very high impedance value), while as soon as the leakage current returns below a certain threshold value, the medical apparatus (the parts thereof connected to the patient) is newly connected to the ground (second configuration with a lower second impedance value). In this way a double effect can be obtained: firstly the medical apparatus effectively disperses the currents leaked during normal operation, in order not to cause disturbances to an electrocardiograph connected to the patient; secondly the medical apparatus can be classified in the CF category (Cardiac Floating) of the standards relating to electrical safety of medical apparatus, since the leakage currents are guaranteed never to exceed the prescribed threshold value which determines that a medical apparatus can be CF classified.

Both the sensor 18 and the selector 20, and the interaction system connecting the two together can be made in various ways. For example, the sensor 18 can comprise one or more current and/or voltage sensors. The selector 20 can comprise one or more switches (for example commanded by one or more solenoid drivers) to selectively connect either one or the other or various resistances to the grounding line 19. The selector 20 can comprise one or more switches (for example commanded by one or more solenoids) to selectively connect or disconnect one or more resistances to the grounding line 19. The selector 20 can comprise one or more switches (for example commanded by one or more solenoids) to selectively open or close one or more bypass lines to bypass one or more resistances connected to the grounding line 19. The interaction system connecting the sensor 18 to the selector 20 can comprise a control algorithm which is operated by a specially-programmed controller provided for this purpose. The interaction system connecting the sensor 18 to the selector 20 can comprise a part of an integrated circuited configured to activate the selector 20 in the desired mode as described herein.

Figure 5:
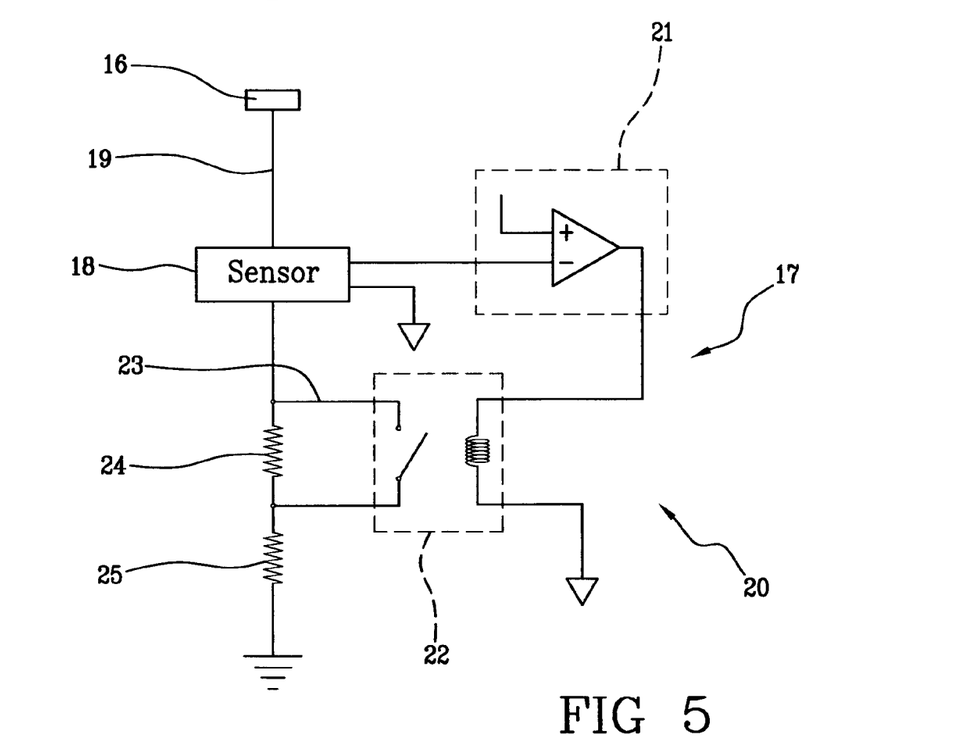
FIG. 5 is a second embodiment of the grounding device usable in the medical apparatus of the present invention.

FIG. 5 shows a grounding device 17 of the present invention, in which the elements which are the same as the device of FIG. 4 have been denoted using the same numbers. In this embodiment the grounding device 17 comprises a comparator 21 which receives a signal from the sensor 18 and compares it with a reference signal. The comparator 21 is connected to a switch 22 operating on a by-pass line 23 for bypassing a first resistance 24 arranged on the grounding line 19. As in the illustrated embodiment, a second resistance 25 can be predisposed (for example a second resistance having a lower value than the first resistance 24). In a specific embodiment, the first resistance 24 can be comprised between 4 and 6 MΩ and the second resistance can be comprised between 1 and 1.5 MΩ. The comparator 21 can be configured to open the by-pass line 23 if the current along the grounding line exceeds a predetermined value, for example a value of between 30 and 50 μA. The above-cited resistance values and threshold values are indicative. Other values could be used for the purpose, for example, of realizing a medical apparatus classifiable within the CF rating which at the same time is able to significantly eliminate the disturbances caused to an electrocardiograph generated by the functioning of the apparatus (in particular due to electrical charges generated by peristaltic pumps), thanks to the grounding device 17 when in the open by-pass 23 configuration.

Figure 6:
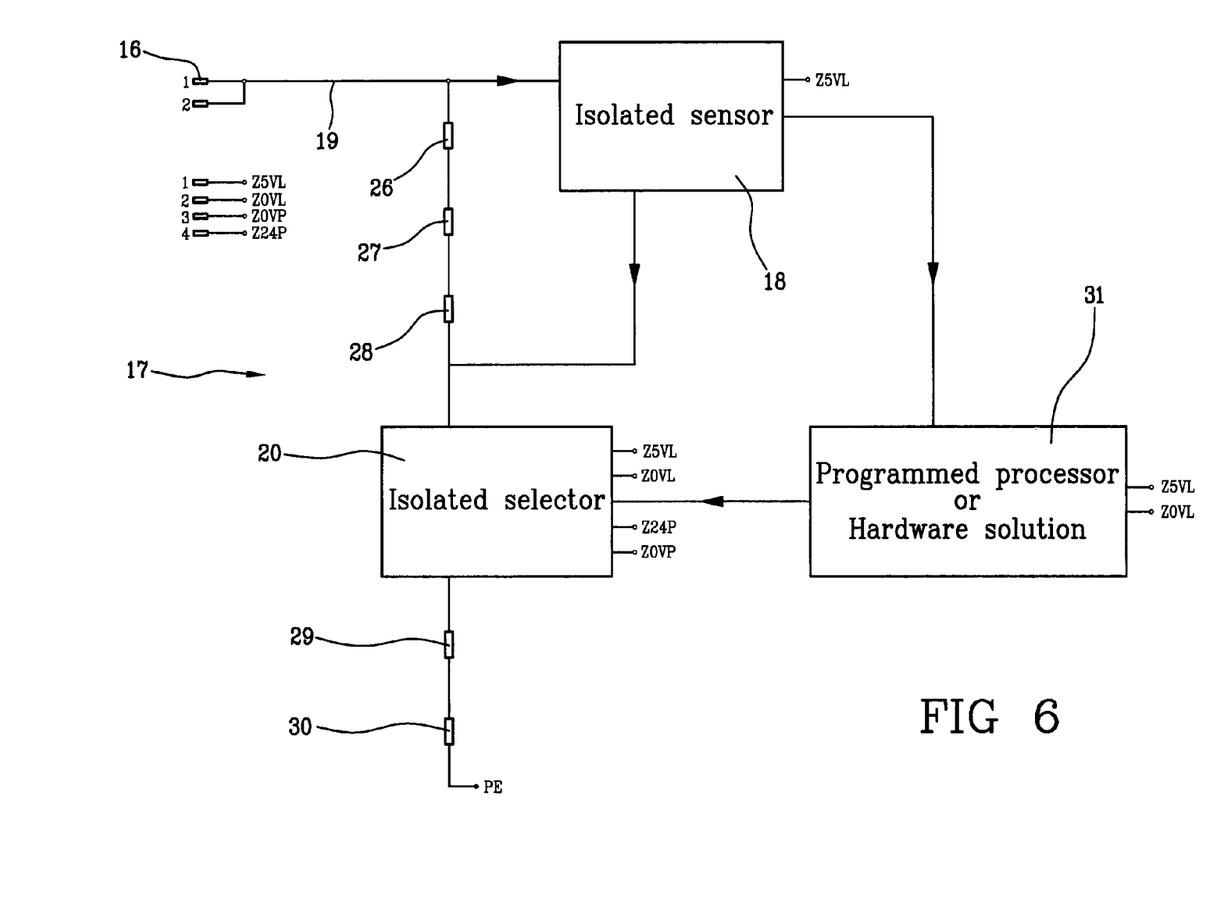
FIG. 6 is a third embodiment of the grounding device usable in the medical apparatus of the invention.

FIG. 6 illustrates a further embodiment of the grounding device 17, in which the elements which are the same as those in FIGS. 4 and 5 have been denoted using the same numbers. In this case the grounding line 19 is provided with a series of resistances (for example five resistances numbered from 26 to 30). In the specific embodiment, resistances numbered from 26 to 29 have a value of 560 KΩ, while resistance 30 has a value of 1 MΩ. 31 schematically denotes a system of interrelation between the sensor 18 and the selector 20. The interrelation system 31 is configured to activate the selector 20 according to the parameter detected by the sensor 18. In particular the interrelation system 31 is designed to cause the selector 20 to assume a first configuration if the sensor detects that a certain parameter, indicative of the voltage on (and/or of the current in) the grounding line 19, is above the mentioned threshold value. In the first configuration the electrical resistance along the grounding line 19 is relatively high (for example so that the medical apparatus can be CF-classified), while in the second configuration the electrical resistance along the grounding line 19 is relatively low (for example with the aim of discharging to the ground the currents which might disturb a further medical device applied to the patient, for example in particular an electrocardiogram or a further measuring or monitoring device). The interrelation system 31 can comprise a hardware system (for example a part of an electrical circuit) and/or a software system (for example an algorithm which is operated by a control processor of the selector 20). In the case of a software system, the processor can be programmed to perform the following stages: a) storing a predetermined threshold value in order to discriminate a risk situation for the electrical safety of the patient 1; b) receiving the signal emitted by the sensor 18; c) checking whether or not the signal emitted by the sensor indicates that the patient is in an electrically safe situation (this stage can comprise, for example, a comparison of the value measured by the sensor 18 with the threshold value stored in the memory; both the measured value and the threshold value can be, for example, indicators of the current dispersed in the patient 1 or in the medical apparatus connected to the patient); d) operating the selector 20 so that the grounding device 17 selectively assumes a configuration of greater ground-insulation if the controls reveal that the patient is in an electrical risk situation, or a configuration of lesser ground-insulation if the controls reveal that the patient is in a situation of electrical safety.

Figure 7:
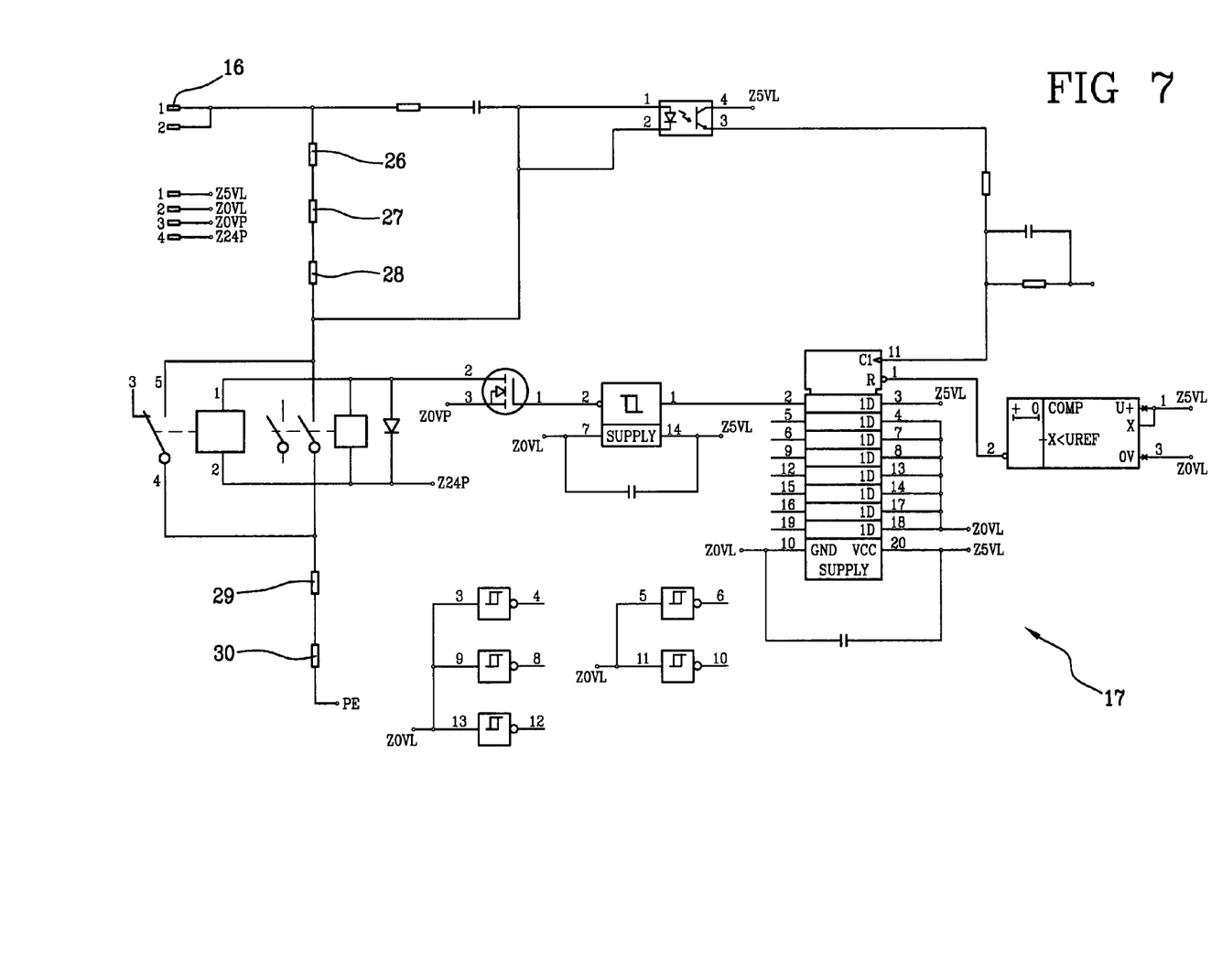
FIG. 7 is a fourth embodiment of the grounding device usable in the medical device of the invention.

FIG. 7 illustrates a specific embodiment of the grounding device 17 of FIG. 6. The elements which are the same as in figures from 4 to 6 have the same numbers. The diagram of FIG. 7 is realized using the known electrical symbols, so no further explanation is required.

Figure 2:
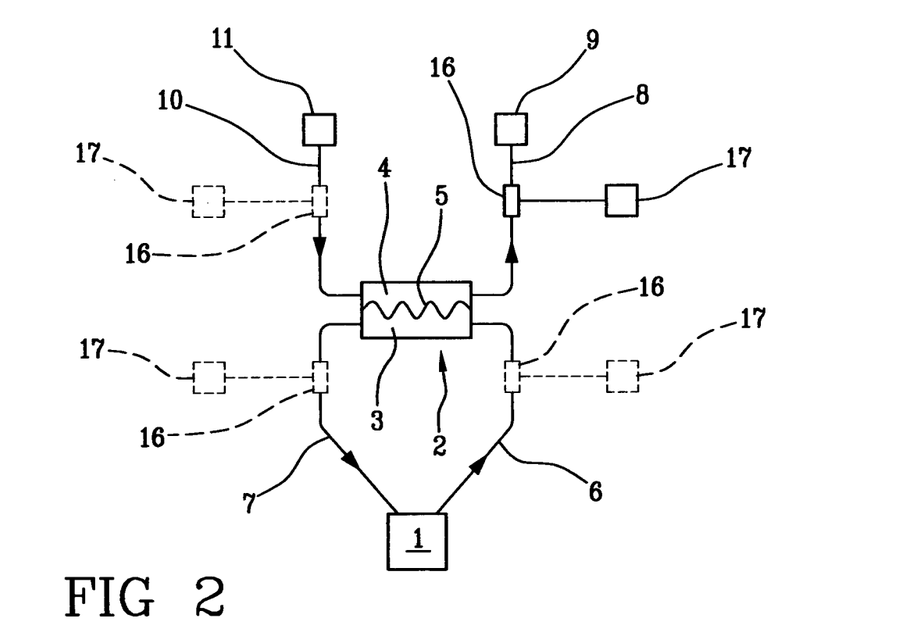
FIG. 2 is a second embodiment of the medical apparatus of the present invention.

FIG. 2 illustrates a further example of a medical apparatus which can use either of the above-described grounding devices 17. In particular the apparatus of FIG. 2 comprises an apparatus for dialysis in which the elements which are the same as in FIG. 1 have been denoted using the same numbering. The electrically-conductive tubular connector 16 is inserted in the discharge line 8 of the used dialysis fluid. The grounding device 17 (any one of those described herein above) is connected to the tubular connector 16. In substitution for, or in addition to, the connector 16 and the device 17 connected to the discharge line 8, the following can be used: a connector and a device 17 connected to the supply line 10 of the fresh dialysis fluid (denoted with a broken line in FIG. 2), and/or a connector 16 and a device 17 connected to the withdrawal line 6 of the blood to be dialyzed (denoted by broken lines in FIG. 2), and/or a connector 16 and a device 17 connected to the return line 7 of the dialyzed blood (denoted by a broken line in FIG. 2).

Figure 3:
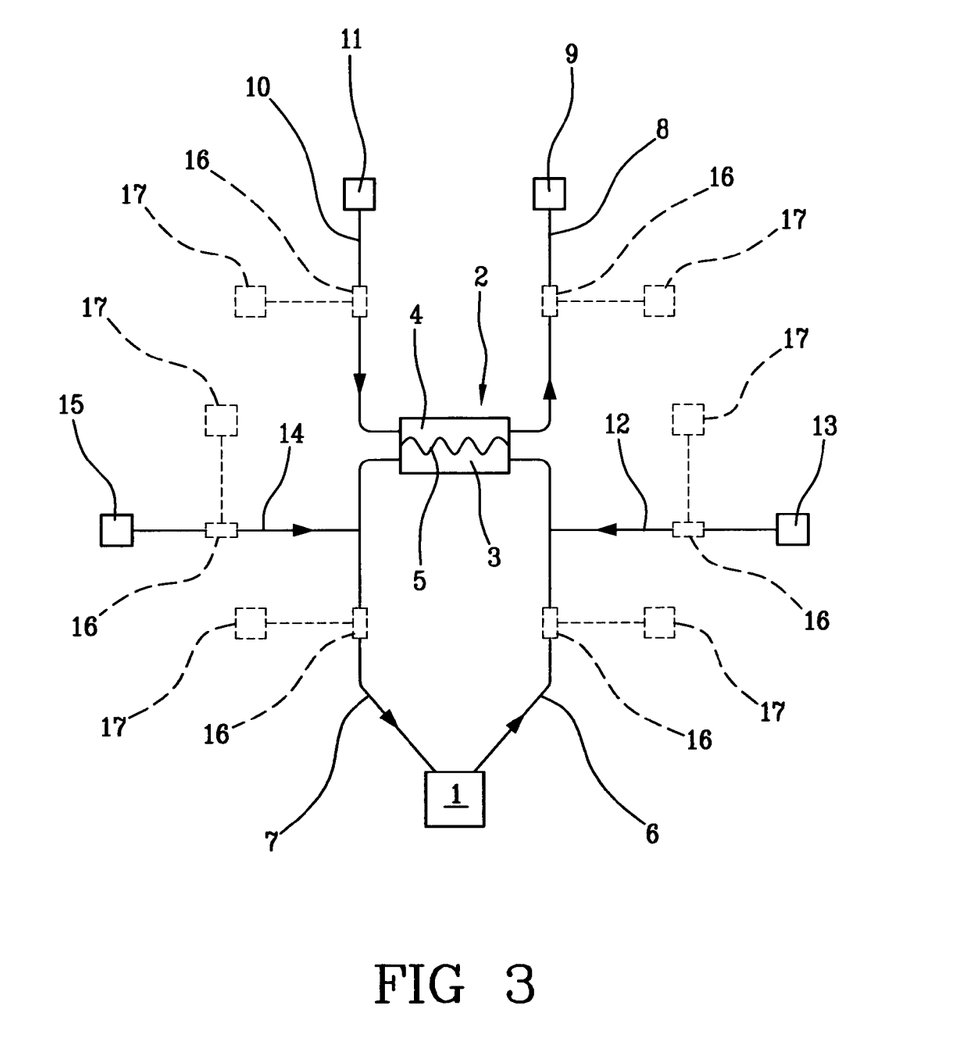
FIG. 3 is a third embodiment of the medical apparatus of the present invention.

FIG. 3 illustrates a further medical apparatus which uses at least one of the above-described grounding devices 17. The apparatus of FIG. 3 is a hemodiafiltration apparatus. In this case too the elements which are the same as in FIGS. 1 and 2 have been denoted using the same numbering. The hemodiafiltration apparatus of FIG. 3 is configured to infuse an infusion liquid (for example a substitution liquid) both in pre-dilution (before the membrane device 2) and in post-dilution (after the membrane device 2). However the hemodiafiltration apparatus can be designed to operate only in pre-dilution or only in post-dilution. The tubular connection 16 and the grounding device 17 can be connected to one or more of the following lines: the withdrawal line 6 of the blood to be treated, the return line 7 of the treated blood, the supply line 10 of the fresh treatment fluid, the discharge line 8 of the used treatment fluid, the upstream infusion line 12, the downstream infusion line 14.

Figure 8:
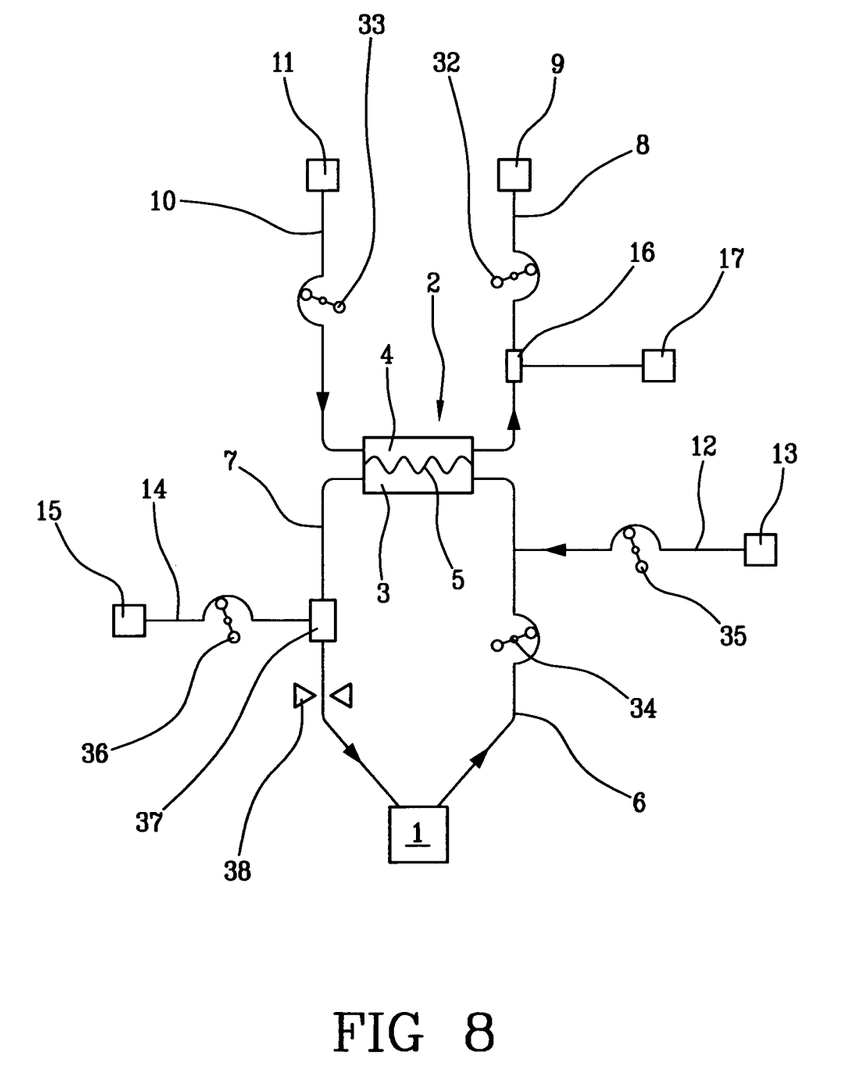
FIG. 8 is a fourth embodiment of the medical apparatus of the present invention.

FIG. 8 illustrates a specific case of the apparatus of FIG. 3, in which the elements which are the same as in FIG. 3 have been denoted using the same numbers. The medical apparatus of FIG. 8 (a hemodiafiltration apparatus) comprises a discharge pump 32 for the movement of the fluid on the discharge line 8. The discharge pump 32 can comprise, for example, a peristaltic pump. The tubular connector 16 is arranged between the discharge pump 32 and the membrane device 2. The medical apparatus further comprises a supply pump 33 (for example a peristaltic pump) moving the fluid on the supply line 10, a blood pump 34 (for example a peristaltic pump) operating (for example on the withdrawal line 6) for moving the blood along the extracorporeal blood circuit, a first infusion pump 35 (for example a peristaltic pump) for moving an infusion fluid (for example an anticoagulant fluid, or a pre-dilution substitution fluid, or a medical fluid) on the upstream infusion line 12, a second infusion pump 36 (for example a peristaltic pump) operating for moving an infusion fluid (for example a post-dilution substitution fluid, or a medical fluid) on the downstream infusion line 14. The extracorporeal blood circuit is provided with an air-blood separation chamber 37 arranged on the return line 7 and a block valve 38 commanded by a control unit and operating on the return line 7 after the separation chamber 37.

It is stressed that the extracorporeal blood circuits of the medical apparatus described herein above can comprise any of the extracorporeal blood circuits of known type used in an extracorporeal blood treatment for kidney failure (for example hemodialysis or hemo(dia)filtration). The circuits can be provided with various elements (for example pressure sensors, hematocrit sensors, air-bubble sensors, block valves, return or injection points, auxiliary lines, etc.) which have not been described in detail.

Each of the above-described grounding devices 17 can be operatively associated with an infusion apparatus, for example such as one of the infusion apparatus described or claimed in the patent publication WO 2004/108206 (with reference to FIG. 14 or claim 36) which are incorporated herein for reference.

All the above-described grounding devices 17 are configured such that during operation, when the sensor 18 detects a risk situation for the electrical safety of the patient 1, the selector 20 assumes a configuration of greater impedance toward the ground (a greater ground-insulation configuration), while when the sensor 18 detects a situation of electrical safety for the patient 1, the selector 20 assumes a configuration of lower ground-impedance (lesser ground-insulation configuration).

Legend
1 Patient
2 Membrane device
3 Blood chamber
4 Fluid chamber
5 Semipermeable membrane
6 To be treated blood withdrawal line
7 Treated blood return line
8 Used fluid discharge line
9 Drainage
10 Fresh treatment fluid supply line
11 Fresh fluid supply source
12 Infusion line upstream of the membrane device
13 Infusion fluid source
14 Infusion line downstream of the membrane device
15 Infusion fluid source
16 Electrically-conductive tubular connector
17 Grounding device
18 Sensor
19 Grounding line
20 Selector
21 Comparator
22 Switch or check valve
23 By-pass line
24 First resistance
25 Second resistance
26 Resistance
27 Resistance
28 Resistance
29 Resistance
30 Resistance
31 Inter-relation system between sensor 18 and sensor 20
32 Discharge pump
33 Supply pump
34 Blood pump
35 First infusion pump
36 Second infusion pump
37 Air-blood separation chamber
38 Block valve (venous clamp)

The invention claimed is:
1. A medical apparatus, comprising:
at least one transport element configured to transport at least one fluid, said transport element being configured to be connected to a patient;
a grounding device connected to the transport element;
a selector designed to vary the effectiveness of the grounding device as a function of a leakage electrical current in at least one of the transport element and the patient wherein the selector comprises a first impedance and a second impedance having different values, the selector being effective to selectively connect a grounding line to the first impedance or the second impedance;
a sensor connected to the selector and effective to emit a signal indicative of a leakage electrical current in at least one of the transport element and the patient; and
a circuit configured to operate the selector as a function of the signal emitted by the sensor, wherein the circuit comprises:
a comparator configured to verify whether the signal emitted by the sensor indicates that the leakage electrical current is greater than a threshold value, and
an operator configured to operate the selector such as that when said signal indicates that the leakage electrical current is less than the threshold value, the selector assumes a first configuration in which the connection between the medical apparatus and the ground has a first impedance value, while when said signal indicates that the leakage electrical current is greater than the threshold value, the selector assumes a second configuration in which the connection between the medical apparatus and the ground has a second impedance value which is greater than the first.

2. The apparatus of claim 1, wherein the transport element comprises:
  a membrane device for extracorporeal blood treatment, the membrane device comprising a blood chamber, a fluid chamber, and a semipermeable membrane separating the blood chamber from the fluid chamber;
  a blood circuit connected to the blood chamber and designed to be connected to a patient; and
  a fluid circuit connected to the fluid chamber;
  the grounding device being connected to at least one of the membrane device, the blood circuit, and the fluid circuit.

3. The apparatus of claim 2, wherein the fluid circuit comprises a discharge line designed to discharge used fluid from the fluid chamber.

4. The apparatus of claim 3, wherein the grounding device has an apparatus end connected to the discharge line.

5. The apparatus of claim 2, wherein the fluid circuit comprises a supply line designed to supply fresh fluid to the fluid chamber.

6. The apparatus of claim 5, wherein the grounding device has an apparatus end connected to the supply line.

7. The apparatus of claim 2, wherein the blood circuit comprises a withdrawal line designed to transfer blood to be treated from the patient to the blood chamber.

8. The apparatus of claim 7, wherein the grounding device has an apparatus end connected to the withdrawal line.

9. The apparatus of claim 2, wherein the blood circuit comprises a return line designed to transfer treated blood from the blood chamber to the patient.

10. The apparatus of claim 9, wherein the grounding device has an apparatus end connected to the return line.

11. The apparatus of claim 2, wherein the grounding device comprises a grounding line having an apparatus end and a ground end, the apparatus end being engaged to at least one of the membrane device, the blood line, and the fluid line.

12. The apparatus of claim 1, wherein the grounding device comprises an electrically conductive part inserted into a flow path of the transport element.

13. The apparatus of claim 1, wherein the grounding device comprises a grounding line having an apparatus end and a ground end, the apparatus end being connected to the transport element.

14. The apparatus of claim 13, wherein the apparatus end comprises an electrically conductive tubular part inserted into a flow path of the transport element.

15. The apparatus of claim 1, configured to perform one or more of the following treatments: hemodialysis, hemofiltration, hemodiafiltration, pure ultrafiltration, hemoperfusion, therapeutic plasma exchange, hepatic failure treatment.

16. A medical apparatus, comprising:
  at least one transport element configured to transport at least one fluid, said transport element being configured to be connected to a patient;
  a grounding device connected to the transport element;
  a selector designed to vary the effectiveness of the grounding device as a function of a leakage electrical current in at least one of the transport element and the patient;
  a sensor connected to the selector and effective to emit a signal indicative of a leakage electrical current in at least one of the transport element and the patient;
  a processor configured to operate the selector as a function of the signal emitted by the sensor, wherein the processor is configured to perform the following steps:
    storing a predetermined threshold value in order to discriminate between a risk situation and safety for a patient;
    receiving the signal emitted by the sensor;
    comparing the signal measured by the sensor with the threshold value stored in the memory;
    operating the selector so that the grounding device selectively assumes a configuration of greater ground-insulation if the comparing reveals that the patient is in a risk situation, or a configuration of lesser ground-insulation if the controls reveal that the patient is in a safety situation.

17. The apparatus of claim 16, wherein the transport element comprises:
  a membrane device for extracorporeal blood treatment, the membrane device comprising a blood chamber, a fluid chamber, and a semipermeable membrane separating the blood chamber from the fluid chamber;
  a blood circuit connected to the blood chamber and designed to be connected to a patient; and
  a fluid circuit connected to the fluid chamber;
  the grounding device being connected to at least one of the membrane device, the blood circuit, and the fluid circuit.

18. The apparatus of claim 17, wherein the fluid circuit comprises a discharge line designed to discharge used fluid from the fluid chamber and wherein the grounding device has an apparatus end connected to the discharge line.

19. The apparatus of claim 17, wherein the fluid circuit comprises a supply line designed to supply fresh fluid to the fluid chamber and wherein the grounding device has an apparatus end connected to the supply line.

20. The apparatus of claim 17, wherein the blood circuit comprises a withdrawal line designed to transfer blood to be treated from the patient to the blood chamber and wherein the grounding device has an apparatus end connected to the withdrawal line.

21. The apparatus of claim 17, wherein the blood circuit comprises a return line designed to transfer treated blood from the blood chamber to the patient and wherein the grounding device has an apparatus end connected to the return line.

22. The apparatus of claim 17, wherein the grounding device comprises a grounding line having an apparatus end and a ground end, the apparatus end being engaged to at least one of the membrane device, the blood line, and the fluid line.

23. The apparatus of claim 16, wherein the grounding device comprises an electrically conductive part inserted into a flow path of the transport element.

24. The apparatus of claim 16, wherein the grounding device comprises a grounding line having an apparatus end and a ground end, the apparatus end being connected to the transport element and wherein the apparatus end comprises an electrically conductive tubular part inserted into a flow path of the transport element.

25. The apparatus of claim 16, wherein the selector comprises a first impedance and a second impedance having different values, the selector being effective to selectively connect a grounding line to the first impedance or the second impedance.

* * * * *